US 8,215,192 B2

(12) United States Patent
Erez et al.

(10) Patent No.: US 8,215,192 B2
(45) Date of Patent: Jul. 10, 2012

(54) SWEAT COLLECTORS AND METHODS OF COLLECTING SWEAT

(76) Inventors: Mordechai Erez, Tel-Aviv (IL); Yaacov Kroin, RaAnana (IL); Zvi Zaykovsky, Tel-Aviv (IL)

( * ) Notice: Subject to any disclaimer, the term of this patent is extended or adjusted under 35 U.S.C. 154(b) by 291 days.

(21) Appl. No.: 12/699,075

(22) Filed: Feb. 3, 2010

(65) Prior Publication Data
US 2010/0132485 A1 Jun. 3, 2010

Related U.S. Application Data

(63) Continuation-in-part of application No. PCT/IL2008/001064, filed on Aug. 3, 2008.

(30) Foreign Application Priority Data

Aug. 6, 2007 (IL) .......................................... 185062

(51) Int. Cl.
*G01N 1/00* (2006.01)
(52) U.S. Cl. ..................................... 73/864.33; 600/578
(58) Field of Classification Search ........................ None
See application file for complete search history.

(56) References Cited

U.S. PATENT DOCUMENTS

| | | | |
|---|---|---|---|
| 3,929,412 A | 12/1975 | Villari | |
| 4,190,060 A * | 2/1980 | Greenleaf et al. ............ | 600/573 |
| 4,266,556 A | 5/1981 | Barlow et al. | |
| 4,448,188 A | 5/1984 | Loeb | |
| 4,452,751 A * | 6/1984 | McCullough et al. ....... | 264/45.5 |
| 4,457,748 A | 7/1984 | Lattin et al. | |
| 4,635,488 A * | 1/1987 | Kremer ........................ | 73/864.72 |
| 4,756,314 A | 7/1988 | Eckenhoff et al. | |
| 5,050,604 A | 9/1991 | Reshef et al. | |
| 5,192,691 A * | 3/1993 | Quinn et al. .................. | 436/161 |
| 5,611,782 A | 3/1997 | Haedt | |
| 6,045,541 A * | 4/2000 | Matsumoto et al. .......... | 604/313 |
| 2002/0055728 A1 | 5/2002 | Finch et al. | |
| 2005/0106750 A1 | 5/2005 | Tung et al. | |
| 2008/0139962 A1* | 6/2008 | Jehanli et al. ................. | 600/573 |

FOREIGN PATENT DOCUMENTS
WO  WO 2009/019686  2/2009

OTHER PUBLICATIONS

International Search Report Dated Jan. 9, 2009 From the International Searching Authority Re.: Application No. PCT/IL2008/001064.
Written Opinion Dated Jan. 9, 2009 From the International Searching Authority Re.: Application No. PCT/IL2008/001064.

* cited by examiner

Primary Examiner — Robert R Raevis

(57) ABSTRACT

A sweat collector for application to a body part of a subject in order to collect sweat therefrom for purposes of analysis, includes a receptacle having an open side for application to the skin of the subject's body part from which the sweat is to be collected; and a port for the introduction of a fluid into the receptacle and into contact with the skin of the subject's body part for enhancing the removal and/or production of sweat thereat. The sweat collector further includes a syringe having an open end insertable into the port for introducing the fluid into the receptacle, and for removing the introduced fluid and the sweat collected therein for analysis. Several embodiments are described, illustrating various ways of attaching the sweat collector to various body parts. Also described is a method of collecting and analyzing sweat from a body part in order to provide information useful in determining the medical condition of a subject.

37 Claims, 6 Drawing Sheets

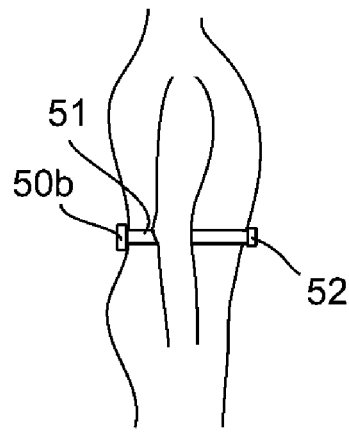
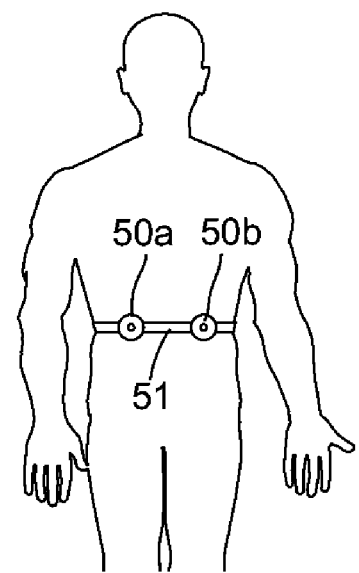
FIG. 7    FIG. 8
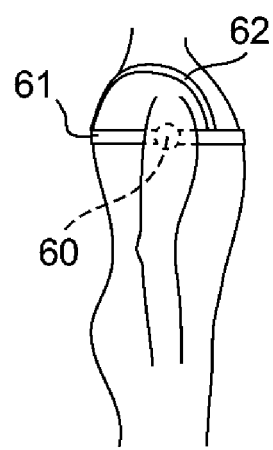
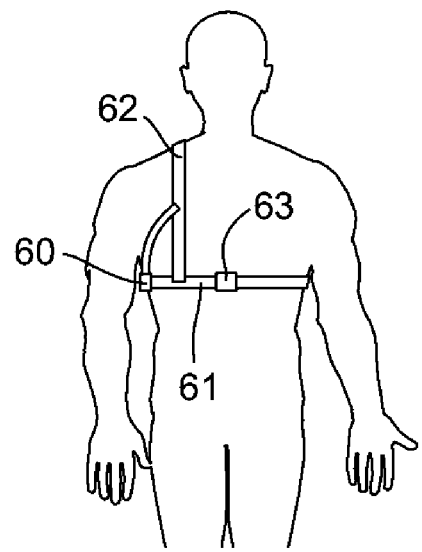
FIG. 9    FIG. 10

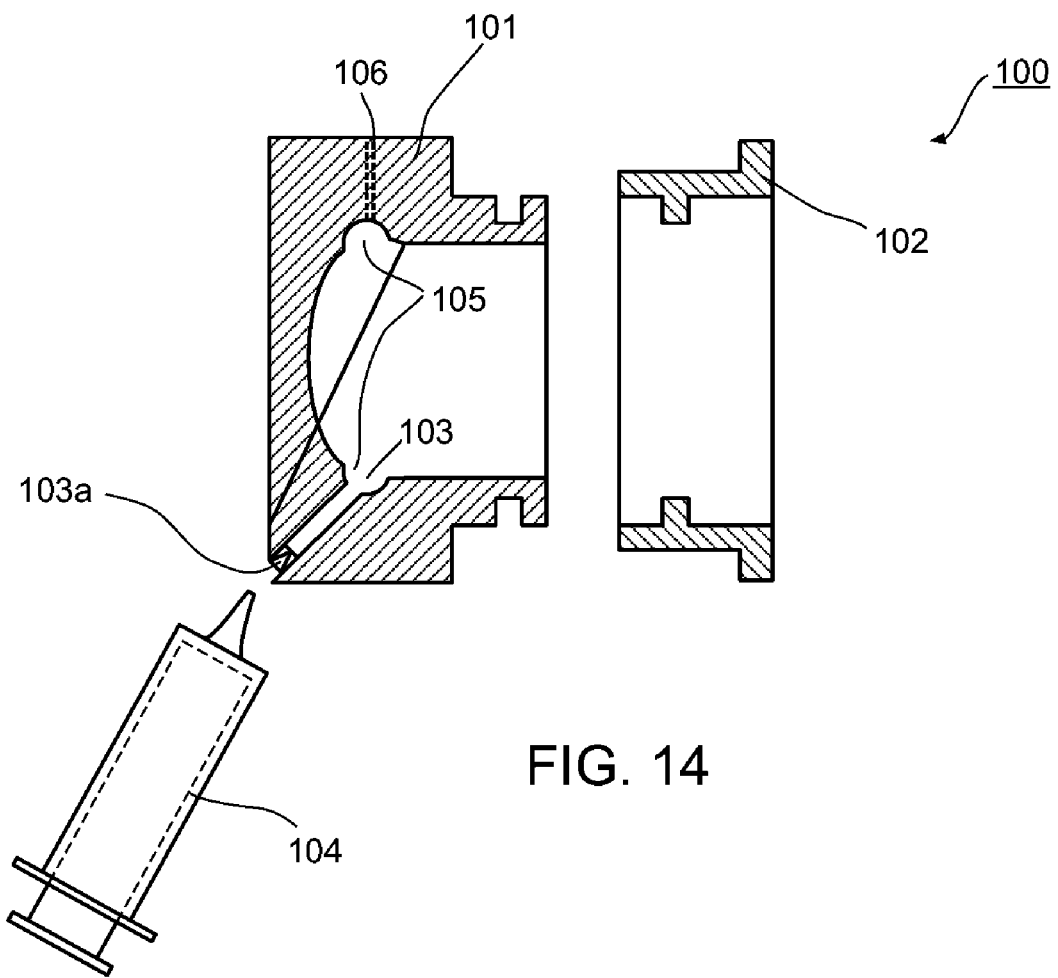
FIG. 14
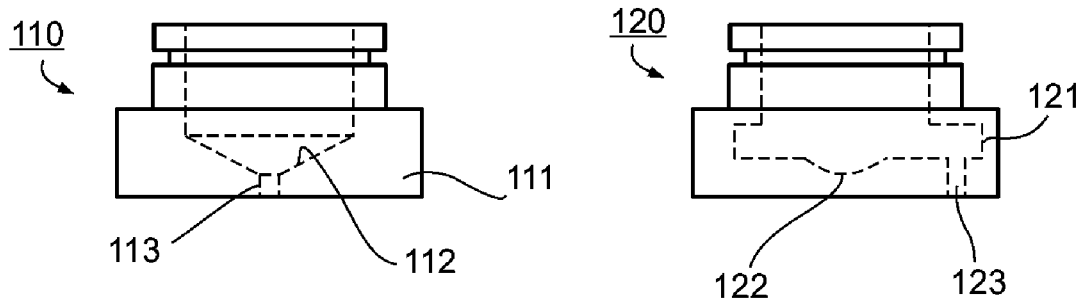
FIG. 15
FIG. 16

SWEAT COLLECTORS AND METHODS OF COLLECTING SWEAT

RELATED APPLICATIONS

This application is a continuation-in-part of PCT Application No. PCT/IL2008/001064 filed on Aug. 3, 2008, and of Israel Patent Application No. 185062 filed on Aug. 6, 2007, the contents of which applicators are incorporated herein by reference.

FIELD AND BACKGROUND OF THE INVENTION

The present invention relates to sweat collectors for application to a body part of a subject in order to collect sweat therefrom for purposes of analysis. The invention also relates to methods of collecting and analyzing sweat in order to provide information useful in determining the medical condition of a subject.

The human body has two kinds of sweat glands, eccrine and apocrine sweat glands. Eccrine sweat glands secrete an aqueous solution of electrolytes (sodium chloride), urea, other metabolites and other organic compounds (e.g., lactic acid). These substances are secreted onto the skin, and are concentrated in certain body parts of the subject, particularly in the forehead and the palms of the hands, to effectively cool the skin of the subject by evaporative cooling. Apocrine sweat glands are located in hairy regions of the body, such as the armpits and around the groin, and secrete fatty materials and various organic substances, including pheromone hormones, thought to serve a biological function in sexual attraction.

The analysis of eccrine sweat for diagnosis of cystic fibrosis by measuring concentrations of the electrolytes (chloride, sodium, and potassium ions) has long been used in the clinics, as shown for example in U.S. Pat. No. 4,542,751. The analysis of apocrine sweat for diagnosis of various diseases by the use of patches has been proposed, e.g., U.S. Published Patent Application 2003/0199743. However, to date, the analytical results obtained for sweat analysis were not found sufficiently reliable and reproducible for any clinical application apart from cystic fibrosis.

Reference is also made to U.S. Pat. No. 5,050,604, in which the inventor of the present application is one of the joint inventors, disclosing an apparatus and method for monitoring the health condition of a subject in a continuous and non-invasive manner. The apparatus and method described in that patent includes a sweat collector unit and a sweat analyzing device both carried on the subject's body by a body attaching device. Also carried by the body attaching device is a container for a flushing solution that was continuously or periodically introduced into the sweat collector device so as to collect the sweat therein by flushing the skin. This patent also disclosed various health conditions detectable by analyzing the sweat, such as cystic fibrosis. It also disclosed various techniques for enhancing the production of sweat from the sweat glands, the collection of the sweat, and the analysis of the sweat to indicate the health condition of the subject. To simplify the description in the present application, the contents of U.S. Pat. No. 5,050,604 are incorporated herein by reference.

The collector and method described in U.S. Pat. No. 5,050,604 was designed for in situ analysis and not for quick and easy sampling for laboratory analysis.

Various analytical procedures are continuously being developed for analyzing substances in body liquids (namely blood and urine), to provide more accurate indications of the health condition of a person. However, because of the limitations of body-carried devices, such improved analytical procedures at the present time can be best performed in laboratories equipped with such analytical devices, rather than on the body of the subject whose health is being monitored.

OBJECTS AND BRIEF SUMMARY OF THE PRESENT INVENTION

An object of the present invention is to provide a sweat collector which enables sweat to be collected from a subject and delivered to an analytical laboratory for analysis. Such collected sweat may be analyzed in a field analytical kit, or in a remotely located laboratory.

Another object of the present invention is to provide a method of collecting and analyzing sweat in order to provide information useful in determining the medical condition of the subject.

According to a broad aspect of the present invention, there is provided a sweat collector for application to a body part of a subject in order to collect sweat therefrom for purposes of analysis, comprising: a receptacle having an open side for application to the skin of the subject's body part from which the sweat is to be collected, a port for the introduction of a fluid into the receptacle and into contact with the skin for enhancing the removal and/or production of sweat thereat, and a valve normally closing the port; and a syringe for receiving the fluid and having an open end insertable into the port for introducing the fluid into the receptacle; the valve being normally closed, but being automatically opened upon the insertion of the open end of the syringe into the port; the syringe having a manually movable member movable towards the open end of the syringe for introducing the fluid in the syringe into the receptacle for application to the subject's skin, the manually movable member being also movable away from the open end of the syringe to withdraw the fluid, and the sweat collected in the receptacle, into the syringe for analysis.

Preferably, but not necessarily, the receptacle further includes a vent at its upper end for venting to the atmosphere the interior of the receptacle during the introduction of the fluid into the receptacle, and the removal of the fluid and collected sweat from the receptacle.

The invention provides various types of collectors designed for different locations on the body. Thus, relative proportions of eccrine versus apocrine may be obtained for use in a diagnostic procedure according to the respective location of the collector on the body.

According to still another aspect of the present invention, there is provided a method of collecting and analyzing sweat from a body part of a subject in order to provide information useful in determining the medical condition of the subject, the method comprising: applying a sweat collector according the above description to the skin of the subject's body part; flushing the skin with a flushing fluid from the syringe of the sweat collector; drawing the flushing fluid, and the sweat collected therein, back into the syringe; and analyzing the sweat collected in the syringe to provide information useful in determining the medical condition of the subject.

As will be described more particularly below, various types of flushing fluids may be used according to the location of the collector and the type of sweat (i.e., eccrine versus apocrine) desired to be collected in order to provide information useful in determining the specific medical condition of the subject. In addition, samples from various locations can be taken at the same time and can be compared to provide a differential analysis.

Further features and advantages of the invention will be apparent from the description below.

BRIEF DESCRIPTION OF THE DRAWINGS

The invention is herein described, by way of example only, with reference to the accompanying drawings, wherein:

FIGS. 7 and 8 are side and back views, respectively, illustrating one form of mounting a sweat collector to a subject in order to collect sweat from the small of the back of the subject;

FIGS. 9 and 10 are side and front views, respectively, illustrating another mounting structure for mounting the sweat collector in an armpit of the subject;

FIG. 14 is an exploded view illustrating a further form of sweat collector constructed in accordance with the present invention;

FIGS. 15 and 16 illustrate two modifications in the sweat collector of FIG. 14;

It is to be understood that the foregoing drawings, and the description below, are provided primarily for purposes of facilitating understanding the conceptual aspects of the invention and possible embodiments thereof, including what is presently considered to be a preferred embodiment. In the interest of clarity and brevity, no attempt is made to provide more details than necessary to enable one skilled in the art, using routine skill and design, to understand and practice the described invention. It is to be further understood that the embodiments described are for purposes of example only, and that the invention is capable of being embodied in other forms and applications than described herein.

DESCRIPTION OF PREFERRED EMBODIMENTS

Figure 1:
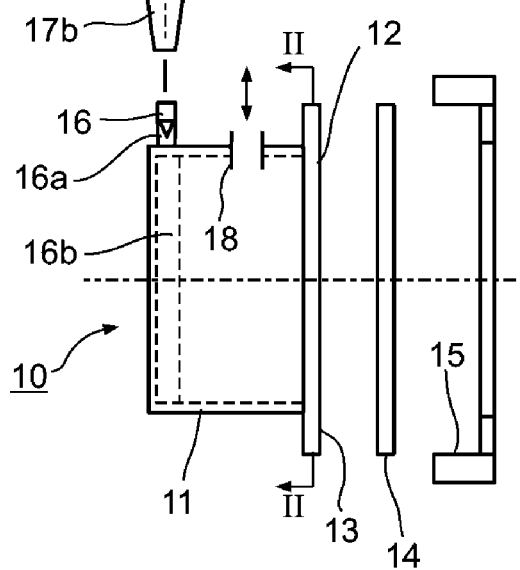
FIG. 1 is an exploded side elevational view illustrating one form of sweat collector constructed in accordance with the present invention.

The sweat collector illustrated in FIG. 1, therein generally designated 10, includes a receptacle 11 of cylindrical configuration and having an open side 12 for application to the skin of the subject's body part from which the sweat is to be collected. Receptacle 11 is further formed with out-turned flange 13 around the periphery of its open side 12 to provide a large surface for contact with the subject's skin.

Figure 11:
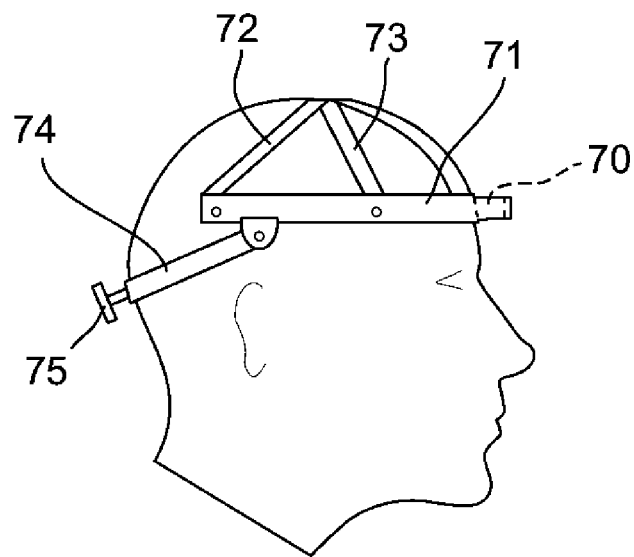
FIGS. 11, 12 and 13 illustrate further mounting arrangements for mounting the sweat collector to the forehead, palm and wrist, respectively, of the subject.

Sweat collector 10 illustrated in FIG. 11 further includes a resilient ring 14 around its flange 13 to permit the open side of the receptacle to conform to the surface of the skin of the body part. For this purpose, resilient ring 14 is carried by the outer surface of flange 13 around the open side of receptacle 11. After the desired amount of sweat has been collected, as will be described more particularly below, the receptacle is closed by a cap 15 applied over flange 13, with the resilient sealing ring 14 therebetween, to seal the contents of the receptacle.

Receptacle 11 further includes a port 16 for the introduction of a flushing fluid into the receptacle and into contact with the skin, for enhancing the removal and/or production of the sweat thereat. For example, the flushing fluid may be a flushing fluid introduced by a syringe 17. In such case, port 16 would be constructed for receiving the open end of the syringe 17 for introducing the fluid into the receptacle. Preferably, port 16 includes a valve 16a which is normally closed but automatically opens upon the insertion of the syringe, and a tube 16b which directs the flushing fluid to the bottom of receptacle 11.

As shown in FIG. 1, syringe 17 includes a tube 17a for receiving a quantity of the flushing fluid to be introduced via port 16, a shaped open end 17b receivable within port 16, and a plunger 17c including a manually operable end 17d projecting from the opposite end of tube 17 for forcing the liquid within the syringe into receptacle 11 via port 16. Preferably, tube 17a is formed with graduated markings 17e to enable predetermined volumes of the fluid to be introduced.

Syringe 17 may be used, not only for introducing the flushing fluid into receptacle 11, but also for withdrawing the flushing fluid, with the sweat, from the receptacle. Thus, the projecting end 17d of plunger 17c may be pressed inwardly to introduce liquid into the receptacle, and may be withdrawn outwardly to draw the liquid, with the sweat, from the interior of the receptacle back into the syringe.

Receptacle 11 may further include an air vent 18, at its upper end, to permit exit of air from the interior of receptacle 11 when the liquid is introduced therein by the syringe, and to allow the entry of air into the receptacle when the liquid and sweat are withdrawn therefrom back into the syringe.

Many different types of liquids, or other fluids, may be introduced into receptacle 11 via port 16 to enhance the removal of sweat from the skin in contact with the open face of receptacle 11, and/or to enhance the production of sweat thereat. For example, the introduced flushing fluid may be an aqueous-based liquid compatible with eccrine sweat, or an oil compatible with the skin and with apocrine sweat, such as polydimethyl siloxane. The flushing fluid may also be an emulsion of oil and water, or a miscible organic solvent, such as dimethyl sulfoxide (DMSO), present in volume from 1 to 20%, or an aqueous solution that contains surface active materials, i.e., detergents, such as sodium lauryl sulfate present in weight from 1 to 20%.

The flushing fluid may also include an internal standard reference compound for measuring dilution, such as dimethyl sulfoxide (DMSO) present from 1-20% by volume. It may also include sudorific compound that enhances sweat collection, such as pilocarbine nitrate present from 0.1 to 10% by weight. The flushing fluid may also contain local or systemic drugs, cosmetics and/or perfumes. The flushing fluid may also include a substance, such as polysugars or other skin compatible compounds, inducing an osmotic solution pressure to enhance sweat production.

Port 16 may also be used to introduce an inert gas, such as nitrogen, to prevent degradation of the sweat sample captured in receptacle 11 when closed by the cap 15.

Figure 2:
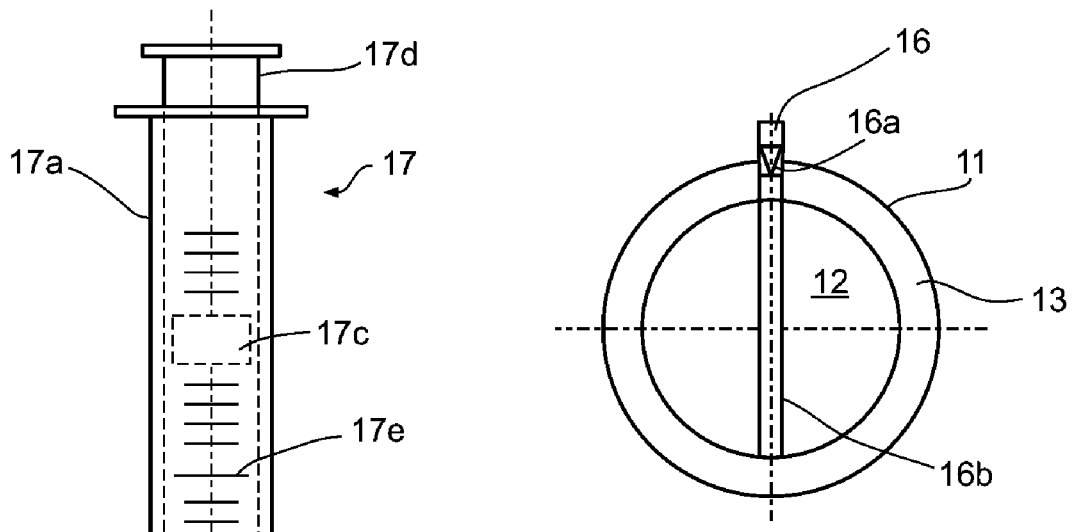
FIG. 2 is a view along line II-II of FIG. 1.
Figure 3:
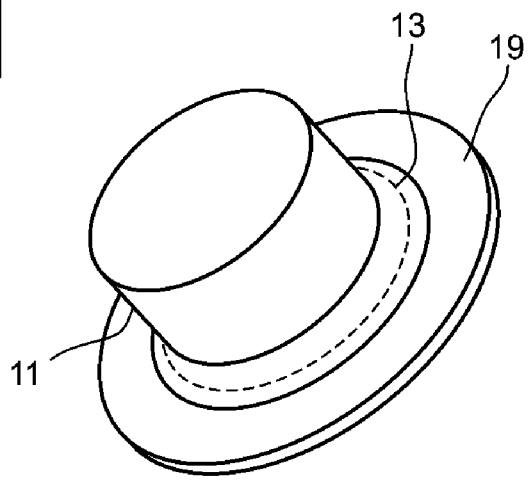
FIG. 3 illustrates one manner of mounting the sweat collector of FIG. 1 to the body of a person in order to collect sweat therefrom.

As indicated earlier, the sweat collector 10 in FIGS. 1 and 2 is intended to be worn by the body of the subject with the open side of receptacle 11 pressed against the subject's body part from which the sweat is to be collected. FIG. 3 illustrates one manner of mounting the receptacle to the subject's body, by the use of an adhesive tape 19 of a shape to enclose the out-turned flange 13 of the receptacle, and to adhesively mount the receptacle via the flange to the skin of the subject's body. FIGS. 7-13 described below illustrate other mounting arrangements that may be used depending on the body part to which the receptacle is to be mounted.

Figure 4:
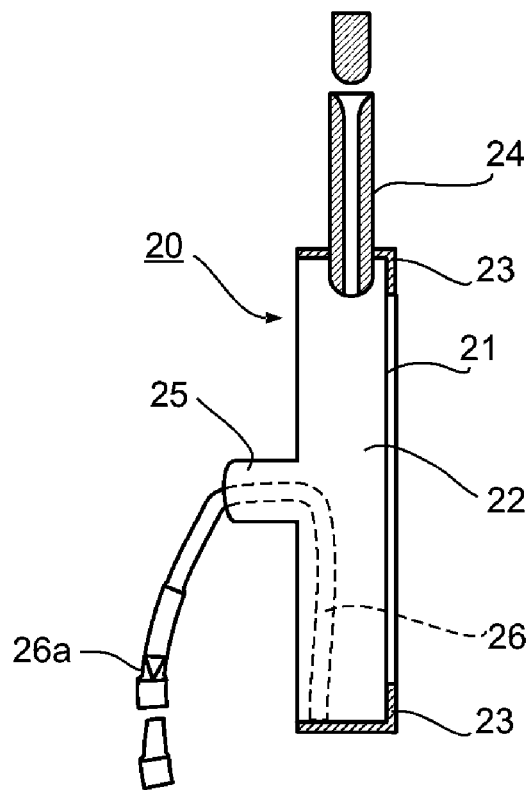
FIG. 4 illustrates another sweat collector constructed in accordance with the present invention.

FIG. 4 illustrates another sweat collector, generally designated 20, constructed in accordance with the present invention. The sweat collector illustrated in FIG. 4 also includes a receptacle 21 having an open side 22 to be applied to the skin of the subject's body part from which the sweat is to be collected. In this case, however, the open side is formed with an in-turned rim 23, rather than an out-turned flange as in FIGS. 1-3. The in-turned rim 23 thus serves the function of the out-turned flange, namely of providing a large surface area to be pressed into contact with the subject's skin. However, since the in-turned rim 23 does not also serve for mounting the receptacle to the subject's body part, another mounting arrangement may be used, such as one of those described below with respect to FIGS. 7-13.

FIG. 4 illustrates another modification, in that receptacle 21 is provided with a separate inlet port 24 for inletting the liquid or other fluid into the receptacle to enhance the removal and/or the production of sweat thereat, and a separate outlet port 25 for removing the liquid with the sweat captured therein for analysis. Port 24 may also serve as an airway for venting the interior, e.g., when drawing out the contents of the receptacle. As seen in FIG. 4, the inlet port 24 is at the upper end of receptacle 21, whereas the outlet port 25 is at an intermediate portion of the receptacle but includes a drain tube 26 having one end extending to the bottom of the interior of the receptacle and an opposite end extending externally of the receptacle to enable efficient flushing and complete removal of its contents. Preferably, the externally extending end includes a one-way valve, as shown at 26a that automatically opens when a syringe or other pump is inserted.

Obviously, port 25 in FIG. 4 can be used both for introducing the fluid from the syringe into the receptacle and for removing the fluid and collected sweat, in which case port 24 would serve as a vent venting the interior of the receptacle to the atmosphere during both the introduction of the fluid into the receptacle and its withdrawal from the receptacle with the collected sweat for analysis.

In all other respects, the construction and manner of use of the sweat collector illustrated in FIG. 4 are substantially the same as described above with respect to FIGS. 1-3.

Figures 5, 6:
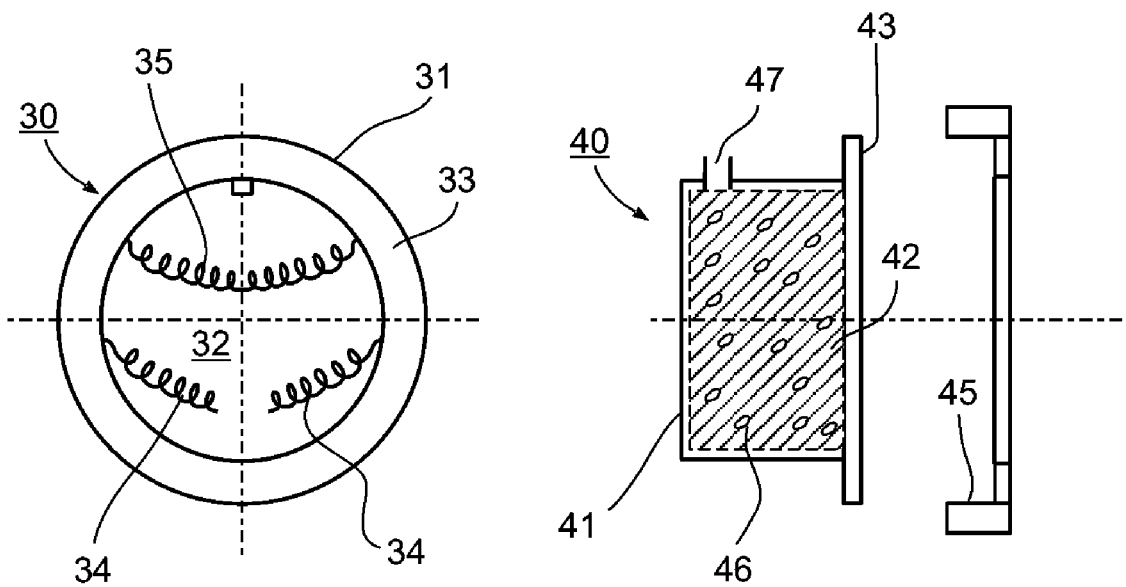
FIG. 5 illustrates a sweat collector including electrodes and/or an electrical heater for enhancing the production of sweat at the collection site, and/or for enhancing the removal of the sweat from the collection site.
FIG. 6 illustrates a further sweat collector which includes an absorbent body for absorbing sweat from the skin at the collection site.

FIG. 5 illustrates another sweat collector, generally designated 30, constructed in accordance with the present invention. The illustrated construction also includes a receptacle 31 having an open side 32 for application to the skin of the subject, and an out-turned flange 33 around the periphery of the open side to provide a large surface for contact with the subject's skin.

Sweat collector 30 illustrated in FIG. 5 further includes electrodes 34 for enhancing the production of sweat in the subject's skin, and/or for examining a physical or chemical property of the collected sweat. For example, electrodes 34 may be iontophoric electrodes which produce sweat stimulation by iontophoresis. In the alternative, the electrodes may be used for measurement of a physical or chemical parameter of the collected sweat, such as conductivity, pH, ionic concentration, etc.

Sweat collector 30 illustrated in FIG. 5 further includes an electrical heater 35 for enhancing the production of sweat by the sweat glands at the site of the sweat collector.

FIG. 6 illustrates a further construction of sweat collector, therein generally designated 40, in accordance with the present invention. Sweat collector 40 also includes a receptacle 41 having an open side 42 circumscribed by an out-turned flange 43 and closable by a cap 45. Sweat collector 40, however, includes, within its interior, a liquid-absorbent porous body 46 for absorbing the sweat produced in the subject's skin enclosed by receptacle 41. Absorbent body 46 may be, for example, a sponge, a foamed material, gauze, cotton wool, or the like.

As shown in FIG. 6, receptacle 41 further includes a port 47 for introducing a fluid, such as one of those described above with respect to FIGS. 1-3, to enhance the removal of sweat from the subject's skin, and/or to enhance the production of the sweat in the subject's skin. Absorbent body 46 should preferably be of a resilient or compressible material, to allow the absorbed liquid, with the sweat collected therein, to be squeezed from the absorbent body for purposes of analysis.

As one preferred example, the absorbent body 46 may be a foamed material such as polyurethane containing a polysugar, such a dextran, present from 0.1-10% by weight of the porous body. Such a body induces an osmotic suction pressure which enhances the removal of the sweat from the surface of the skin.

In all other respects, the structure and manner of use of sweat collector 40 illustrated in FIG. 6 may be substantially as described above with respect to the other embodiments.

FIGS. 7-13 illustrate various arrangements for mounting a sweat collector constructed in accordance with the present invention to a selected body part of the subject in order to collect the sweat thereat. The mounting arrangements illustrated in FIG. 7-13 are particularly useful where the sweat collector is of the in-turned rim construction as described above with FIG. 4, but of course may also be used with the out-turned flange construction illustrated in FIGS. 1-3, 5 and 6, as well as any other appropriate construction.

Thus, FIGS. 7 and 8 illustrate two sweat collectors 50a, 50b mounted to the small of the back of the subject by a waist belt 51 having a buckle or other type of fastener 52 at the front for applying, removing and/or tightening the waist belt.

FIGS. 9 and 10 illustrate sweat collector 60 mounted in an armpit of the subject by a chest belt 61 applied across the upper part of the subject's chest, and a shoulder belt 62 applied around the shoulder of the subject for securing the sweat collector in place. Chest belt 60 further includes a buckle or other type fastener 63 for applying, removing and/ or tightening the chest belt.

FIG. 11 illustrates a sweat collector 70 mounted by a head band 71 against the forehead of the subject. Head band 71 further includes a pair of crossed bands 72, 73 engageable with the upper portion of the subject's head, and a further band 74 including a tightening device 75 for securing the head band 71, and the sweat collector 70 carried thereby, to the subject's head.

Figure 12:
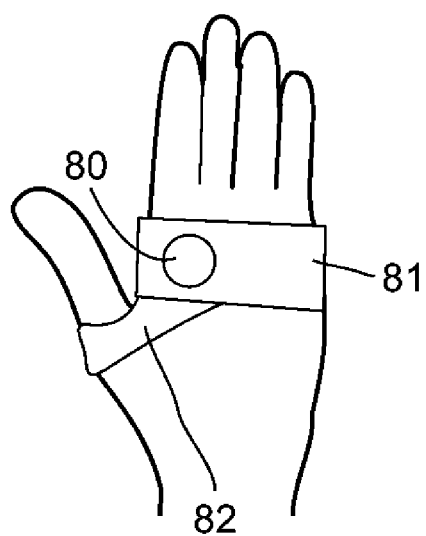

FIG. 12 illustrates a sweat collector 80 secured to the palm of the subject's hand by a first band 81 applied between the thumb and index finger of the subject, and a second band 82 having an opening for receiving the thumb of the subject.

Figure 13:
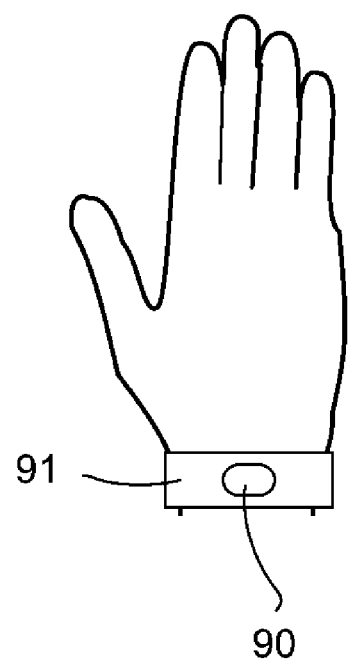

FIG. 13 illustrates a sweat collector 90 applied to the wrist of the subject by a wrist band 91.

FIG. 14 illustrates a sweat collector, generally designated 100, constituted of two parts, namely a main part 101 for receiving the sweat to be collected, and a separate flange part 102 attachable to the open side of the main part 101. The main part 101 is preferably made of a transparent rigid material, such as an acrylic resin, whereas the flange part 102 is preferably made of an elastomeric material, such as a silicone resin, so as to produce a good seal contact when applied against the subject's skin. The main part 101 is formed with the port 103 for introducing a flushing solution, and/or for withdrawing the collected sweat, via a syringe 104. Port 103 is located in a cavity 105 formed in the main part 101 at its lower point when applied to the subject's body so as to enable withdrawing substantially all the collected sweat by the syringe. Port 103 also includes a valve 103a which is normally closed but which automatically opens upon the insertion of the syringe 104. Main part 101 is formed at its upper end with a vent 106 venting its interior to the atmosphere.

FIGS. 15 and 16 illustrate two modifications in the construction of the main part, therein designated 110 and 120, respectively. In FIG. 15, the main part 110 includes a closed wall 111 formed centrally with a cavity 112, and with the port 113 extending centrally of the cavity, so as to remove substantially all the sweat collected therein. In FIG. 16, the main part 120 also includes an end wall 121 formed with a central cavity 122, but in this case the port 123 is formed laterally of the cavity, so as to trap a quantity of the sweat collected therein for later processing if desired. While FIGS. 15 and 16 (also FIG. 14) illustrate the sweat collector as being made of two parts, it will be appreciated it could be constructed as a single part.

Figure 17:
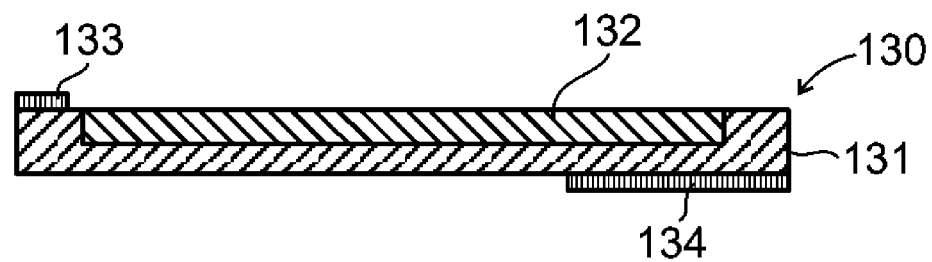
FIG. 17 is a sectional view illustrating an external heater which may be used for enhancing the production of sweat at the examined body part.
Figure 18:
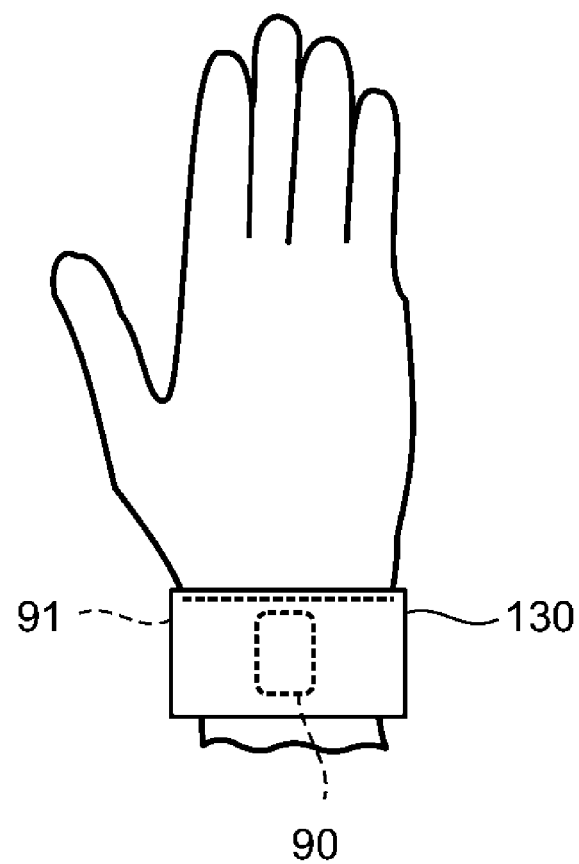
FIG. 18 illustrates the external heater of FIG. 17 applied to the collector applied to the subject's wrist as illustrated in FIG. 13.

FIGS. 17 and 18 illustrate a further option of using an external heater for heating the sweat collector when applied to the body part in order to enhance the production of sweat therein.

As shown in FIG. 17, the external heater, therein generally designated 130, includes an insulating base layer 131 carrying on one surface a heater element 132, which may be an electrical heater, a pliable bag filled with hot water or other heating or heat-generating medium, etc. The external heater unit 130 is preferably constructed in the form of a band or the like wrappable about the body part from which the sweat is to be collected, as shown at 130 in FIG. 18, and retained in its wrapped condition by hook-and-loop fastening elements, e.g. hook elements 133 on one face of one end of the band, and loop elements 134 on the opposite face of the other end of the band. It will be appreciated that other types of fasteners could be used, such as buttons, hooks, and snap-fasteners, and that the external heater could be in the form of a sleeve slipped over the respective body part.

The system is mainly aimed for analyzing organic compounds such as lactic acid, glucose, urea, creatinine, amino acids that are known to be present in eccrine sweat, as well as peptide, proteins, etc. in the apocrine sweat, particularly to monitor diabetes or other metabolic diseases or other diseases in general, as well as to detect drugs (legal or illegal).

For purposes of example, we set forth below a number of flushing fluids which can be used for collecting the sweat, and/or for enhancing the sweat production, according to the specific sweat (eccrine, apocrine, or the relative proportions of each) at the body location from which the sweat is collected:

Example 1

As one example, the flushing fluid may be an aqueous solution compatible with the eccrine sweat. Such a flushing fluid would be used, for example, where the receptacle is applied to the forehead or palm of the subject, wherein hair is substantially absent from the skin.

Example 2

This example would be applicable to the collection of apocrine sweat, together with eccrine sweat, when the receptacle would be applied, for example, to the armpit of the subject, the chest of the subject, the small back of the subject, or other area in which the skin contains significant hair. In such an application, the flushing fluid would include an oil compatible with the skin and with apocrine sweat, such as polydimethyl siloxane, and could be in the form of an emulsion of oil and water.

Example 3

The flushing fluid could also include a miscible organic solvent, such dimethyl sulfoxide (DMSO), present in amounts of 1-20% by volume. Such a flushing fluid can also serve as an internal standard reference compound for measuring dilution.

Example 4

Another example of a flushing fluid that can be used is one containing a sudorific compound that enhances sweat collection, such as pilocarpine nitrate, present in 0.1-10% by weight.

Example 5

In any of the foregoing examples, the flushing fluid could also include a local or systemic drug, cosmetic, and/or perfume.

Quantifying or Normalizing Actual Concentration

The actual concentration of the sweat flushed from the skin made by quantified or normalized according to a reference added to the flushing solution. The reference ingredient may be DMSO, as mentioned in Example 3 above.

The electrical conductivity, and/or concentration of the sodium, potassium, chloride and other ions can be used, as well as small organic molecules such as urea and/or lactic acid for use as an internal standard quantifying or normalizing the actual concentrations of the ingredients in the sweat.

The site at which the sweat is removed may be consecutively flushed with the same or different flushing solutions, e.g. first an aqueous solution for eccrine sweat removal, and afterwards, an oily solution, or one containing a surface active agent, for the apocrine sweat removal. Also, samples may be taken simultaneously from different parts of the body to produce a differential comparison, e.g., between eccrine sweat and apocrine sweat.

While the invention has been described with respect to several preferred embodiments, it will be appreciated that these are set forth merely for purposes of example, and that many other variations, modifications and applications of the invention may be made.

What is claimed is:

1. A sweat collector for application to a body part of a subject in order to collect sweat therefrom for purposes of analysis, comprising:
   a receptacle having an open side for application to the skin of the subject's body part from which the sweat is to be collected, a port for the introduction of a fluid into said receptacle and into contact with said skin for enhancing the removal and/or production of sweat thereat, and a valve normally closing said port;

and a syringe for receiving said fluid and having an open end insertable into said port for introducing said fluid into the receptacle;

said valve being normally closed, but being automatically opened upon the insertion of said open end of the syringe into said port;

said syringe having a manually movable member movable towards said open end of the syringe for introducing said fluid in the syringe into said receptacle for application to the subject's skin, said manually movable member being also movable away from said open end of the syringe to withdraw the fluid, and the sweat collected in said receptacle, into said syringe for analysis.

2. The sweat collector according to claim 1, wherein said receptacle further includes a vent at its upper end for venting to the atmosphere the interior of the receptacle during the introduction of said fluid into the receptacle, and the removal of the fluid and collected sweat from the receptacle.

3. The sweat collector according to claim 1, wherein the open side of said receptacle includes a resilient ring around its perimeter to permit the open side of the receptacle to conform to the surface of said skin of the subject and to seal said open side of the receptacle with respect to said skin of the subject.

4. The sweat collector according to claim 1, wherein said receptacle further includes an out-turned flange around the periphery of the open side of the receptacle to provide a large surface for contact with said skin of the subject.

5. The sweat collector according to claim 4, wherein said receptacle is of a two-part construction, including a main part of a transparent material enabling viewing the contents of the receptacle, and a separate flange part formed with said out-turned flange and made of an elastomeric material to produce a seal with said skin of the subject.

6. The sweat collector according to claim 5, wherein the sweat collector further includes an adhesive tape of a shape to enclose said out-turned flange and to adhesively mount the receptacle via said flange to said skin of the subject.

7. The sweat collector according to claim 1, wherein said receptacle further includes a liquid-absorbent porous body for absorbing the introduced fluid, and the sweat removed thereby from said skin of the subject.

8. The sweat collector according to claim 7, wherein said porous body includes a substance which induces an osmotic suction pressure to enhance the production and removal of sweat from said skin of the subject.

9. The sweat collector according to claim 8, wherein said substance is a polysugar present from 0.1-10% by volume of the porous body.

10. The sweat collector according to claim 1, wherein said receptacle includes electrodes for enhancing the production of sweat in said skin of the subject, and/or for examining a physical or chemical property of the collected sweat.

11. The sweat collector according to claim 1, wherein said receptacle includes an electrical heater for enhancing the production of sweat in said skin of the subject.

12. The sweat collector according to claim 1, wherein the sweat collector further includes a body mounting constructed for mounting the receptacle to a selected body part of the subject.

13. The sweat collector according to claim 12, wherein said body mounting is constructed to mount the receptacle to the small of the back of the subject.

14. The sweat collector according to claim 12, wherein said body mounting is constructed to mount the receptacle in an armpit of the subject.

15. The sweat collector according to claim 12, wherein said body mounting is constructed to mount the receptacle to the forehead of the subject.

16. The sweat collector according to claim 12, wherein said body mounting is constructed to mount the receptacle to the palm of a hand of the subject.

17. The sweat collector according to claim 12, wherein said body mounting is constructed to mount the receptacle to the wrist of the subject.

18. The sweat collector according to claim 1, wherein said sweat collector further comprises an external heating element applicable over said receptacle for heating said skin of the subject in order to enhance the production of sweat therein.

19. A method of collecting and analyzing sweat from a body part of a subject in order to provide information useful in determining the medical condition of the subject, said method comprising:

applying a sweat collector according to claim 1 to the skin of the subject's body part;

flushing said skin with a flushing fluid from said syringe of the sweat collector;

drawing said flushing fluid, and the sweat collected therein, back into said syringe;

and analyzing the sweat collected in the syringe to provide information useful in determining the medical condition of the subject.

20. The method according to claim 19, wherein the flushing fluid is an aqueous solution for flushing eccrine sweat.

21. The method according to claim 19, wherein the flushing fluid is an oil for flushing apocrine sweat.

22. The method according to claim 21, wherein said oil is polydimethyl siloxane.

23. The method according to claim 19, wherein the flushing fluid is an emulsion of oil and water.

24. The method according to claim 19, wherein the flushing fluid contains a miscible organic solvent.

25. The method according to claim 24, wherein said miscible organic solvent is dimethyl sulfoxide (DMSO) present from 1 to 20% by volume, which also serves as an internal standard reference compound for measuring dilution.

26. The method according to claim 19, wherein the flushing fluid contains a sudorific compound that enhances sweat secretion.

27. The method according to claim 26, wherein said sudorific compound is pilocarpine nitrate present from 0.1 to 10% by weight.

28. The method according to claim 19, wherein the flushing fluid contains local or systemic drugs, cosmetics or perfumes.

29. The method according to claim 19, wherein the flushing fluid includes a reference ingredient for quantifying or normalizing the sweat collected in the receptacle.

30. The method according to claim 29, wherein said reference ingredient is DMSO.

31. The method according to claim 19, wherein the electrical conductivity, and/or the concentration of, sodium, potassium, chloride or other ions is used for quantifying or normalizing the actual concentration of the ingredients in the collected sweat.

32. The method according to claim 19, wherein urea and/or lactic acid is used for quantifying or normalizing the actual concentration of the ingredients in the collected sweat.

33. The method according to claim 19, wherein said flushing fluid includes an inert gas introduced into the receptacle.

34. The method according to claim 19, wherein the flushing fluid is a liquid containing a surface active material.

35. The method according to claim 34, wherein said surface active material is sodium lauryl sulfate present in weight from 1 to 20%.

36. The method according to claim 19, wherein the site at which the sweat is removed is consecutively flushed with different flushing solutions for the selective removal of eccrine sweat and apocrine sweat, respectively.

37. The method according to claim 19, further including the application of an external heating element over said receptacle for heating the body part in order to enhance the production of sweat therein.

* * * * *